US011583190B2

(12) United States Patent
Shantharam (10) Patent No.: US 11,583,190 B2
(45) Date of Patent: Feb. 21, 2023

(54) METHOD AND SYSTEM FOR INDICATING A BREATHING PATTERN

(71) Applicant: KAHA PTE. LTD., Singapore (SG)

(72) Inventor: Sudheendra Shantharam, Bengaluru (IN)

(73) Assignee: KAHA PTE. LTD., Singapore (SG)

( * ) Notice: Subject to any disclaimer, the term of this patent is extended or adjusted under 35 U.S.C. 154(b) by 240 days.

(21) Appl. No.: 16/959,422

(22) PCT Filed: Dec. 26, 2018

(86) PCT No.: PCT/SG2018/000009
§ 371 (c)(1),
(2) Date: Jun. 30, 2020

(87) PCT Pub. No.: WO2019/132771
PCT Pub. Date: Jul. 4, 2019

(65) Prior Publication Data
US 2020/0329979 A1    Oct. 22, 2020

(30) Foreign Application Priority Data

Dec. 30, 2017 (IN) .............................. 20171 1047438

(51) Int. Cl.
*A61B 5/0205* (2006.01)
*G16H 10/60* (2018.01)
*A61B 5/00* (2006.01)

(52) U.S. Cl.
CPC .......... *A61B 5/0205* (2013.01); *A61B 5/0022* (2013.01); *A61B 5/681* (2013.01); *A61B 5/7246* (2013.01); *A61B 5/742* (2013.01); *A61B 5/746* (2013.01); *G16H 10/60* (2018.01)

(58) Field of Classification Search
CPC ..... A61B 5/0205; A61B 5/0022; A61B 5/681; A61B 5/7246; A61B 5/742; A61B 5/746; A61B 5/0816; G16H 10/60; G04G 9/00; A61M 2021/0088; A61M 2021/0005; A61M 21/00; A61M 21/02
USPC ......................................................... 600/484
See application file for complete search history.

(56) References Cited

U.S. PATENT DOCUMENTS

| | | | | |
|---|---|---|---|---|
| 2010/0312041 | A1* | 12/2010 | Elliott | A61B 5/486 600/27 |
| 2016/0166197 | A1* | 6/2016 | Venkatraman | A61B 5/0816 600/595 |
| 2017/0325771 | A1* | 11/2017 | Tsunomori | G06T 7/0016 |
| 2017/0358239 | A1* | 12/2017 | Arney | A61B 5/0205 |
| 2018/0325422 | A1* | 11/2018 | Sokol | A62B 7/10 |

* cited by examiner

*Primary Examiner* — Jay B Shah
(74) *Attorney, Agent, or Firm* — Perilla Knox & Hildebrandt LLP; Kenneth A. Knox (57) ABSTRACT

A method and system for indicating a breathing pattern is disclosed. The system comprises a plurality of smart wearable devices, a plurality of mobile devices, an application server and a database. The plurality of smart wearable devices is either connected to the mobile devices or directly connected to the application server. The database is connected to the application server to store the data transmitted by the smart wearable device or the mobile device. The plurality of smart wearable devices is capable of monitoring the health index and identifying the variation in health conditions of the user, in real-time and activating a suitable breathing pattern to normalize such medical condition.

19 Claims, 5 Drawing Sheets

METHOD AND SYSTEM FOR INDICATING A BREATHING PATTERN

CROSS-REFERENCE TO RELATED APPLICATION

This application is a national phase application under 35 U.S.C. § 371 of International Application No. PCT/SG2018/000009 filed Dec. 26, 2018, which claims the benefit of and priority to India Patent Application No. 201711047438 filed Dec. 30, 2017.

FIELD OF THE INVENTION

The present disclosure relates generally to the field of monitoring and improving medical and health condition of a user and in particularly relates to methods and systems for indicating a breathing pattern to the user based on monitored condition.

BACKGROUND OF THE INVENTION

A hectic and a chaotic life schedule have gifted human beings many undesirable and nonessential medical and psychological conditions. As a result, human beings face stress, anger, frustration, anxiety and a disturbed emotional environment in a continuous manner. Few people have relied on allopathy medicines to address the disturbed emotional environment. However, the allopathy medicines are not suitable for everyone and typically have some side effects.

Other people have started performing breathing exercises such as Yoga to address such disturbed emotional environment. Generally, these people practice the breathing exercise at a specific interval during a day. Whenever a person experiences the disturbed emotional environment such as anger, the person is required to perform a set of actions which includes breathing exercises to control his anger. Similarly, when the person is going through another medical condition such as the stress, the person can perform another set of actions and related breathing exercises to overcome the stress. At many instances, the person must perform specific breathing exercises regularly so that preventive actions are taken to avoid serious medical conditions such as drastic change or abnormalities in heart rates, blood flow etc.

In view of foregoing discussion, there exists a need for a method and a system for guiding the person to perform the breathing exercise in a real time to encounter the disturbed emotional environment and normalize such emotional environment.

SUMMARY OF THE INVENTION

The present invention provides methods and systems to detect adverse medical conditions of a user using a smart wearable device and to provide a preset actions including breathing patterns to reduce or normalize such conditions of the user. The smart wearable device is a smart watch, wherein hands of the smart watch are configured to notify the breathing pattern to the user.

In an embodiment, a method indicating a breathing pattern to a user is provided. The method includes the steps of: receiving real-time data values corresponding to one or more health based parameters of a user; detecting a variation in real-time data values beyond a pre-defined acceptable range of data values corresponding to each of said one or more health based parameters of the user; determining a type of at least one condition based on said detecting of variation in real-time data values; activating at least one smart wearable device on determining said type of at least one condition; identifying a first breathing pattern from a plurality of pre-defined breathing patterns based on type of said at least one condition, wherein exercising of the first breathing pattern facilitates in bringing the real-time data values corresponding to said one or more health based parameters within said pre-defined acceptable range; and configuring the at least one smart wearable device to display a first visual representation representing the first breathing pattern, wherein the first visual representation includes at least one of an hour hand, a minute hand and a second hand representing arms of the smart wearable (for example, watch), and wherein different cycles of a breath in the first breathing pattern are represented by rotation cycles of the at least one of the hour hand, the minute hand and the second hand respectively.

In another embodiment, a system for indicating a breathing pattern to a user is provided. The system includes a receiving unit configured to receive real-time data values corresponding to one or more health based parameters of a user; a detecting unit configured to detect at least one variation in real-time data values beyond a pre-defined acceptable range of data values corresponding to each of said one or more health based parameters of the user; a monitor configured to determine a type of at least one condition based on said detecting of variation in real-date values; a controller configured to: activate at least one smart wearable device on determining said type of at least one condition; identify a first breathing pattern from a plurality of pre-defined breathing patterns based on type of said at least one condition, wherein exercising of the first breathing pattern facilitates in bringing the real-time data values corresponding to said one or more health based parameters within said pre-defined acceptable range; and configure the at least one smart wearable device to display a first visual representation representing the first breathing pattern, wherein the first visual representation includes at least one of an hour hand, a minute hand and a second hand representing arms of smart wearable (for example, watch), and wherein different cycles of a breath in the first breathing pattern are represented by a pattern or rotation cycles of the at least one of the hour hand, the minute hand and the second hand respectively.

It is object of the invention to provide mechanism for detecting a medical condition of a user by monitoring heart rates (pulse), breathing, movement of hands, blood flow, and other biometric health related parameters of a user.

It is object of the invention to recommend a breathing exercise/pattern that can facilitate in normalizing medical and health conditions of the user.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF FIGURES

These and other features, aspects, and advantages of the present invention will become better understood when the following detailed description is read with reference to the accompanying drawings in which like characters represent like parts throughout the drawings, wherein.

Further, skilled artisans will appreciate that elements in the drawings are illustrated for simplicity and may not have been necessarily been drawn to scale. For example, the flow charts illustrate the method in terms of the most prominent steps involved to help to improve understanding of aspects of the present invention. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION

For the purpose of promoting and understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

It will be understood by those skilled in the art that the foregoing general description and the following detailed description are exemplary and explanatory of the invention and are not intended to be restrictive thereof.

Reference throughout this specification to "an aspect", "another aspect" or similar language means that a particular feature, structure, or characteristic described in connection with the embodiment is included in at least one embodiment of the present invention. Thus, appearances of the phrase "in an embodiment", "in another embodiment" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Unless otherwise defined, all technical and scientific terms used herein have the same meaning as commonly understood by one of ordinary skill in the art to which this invention belongs. The system, methods, and examples provided herein are illustrative only and not intended to be limiting.

Figure 1:
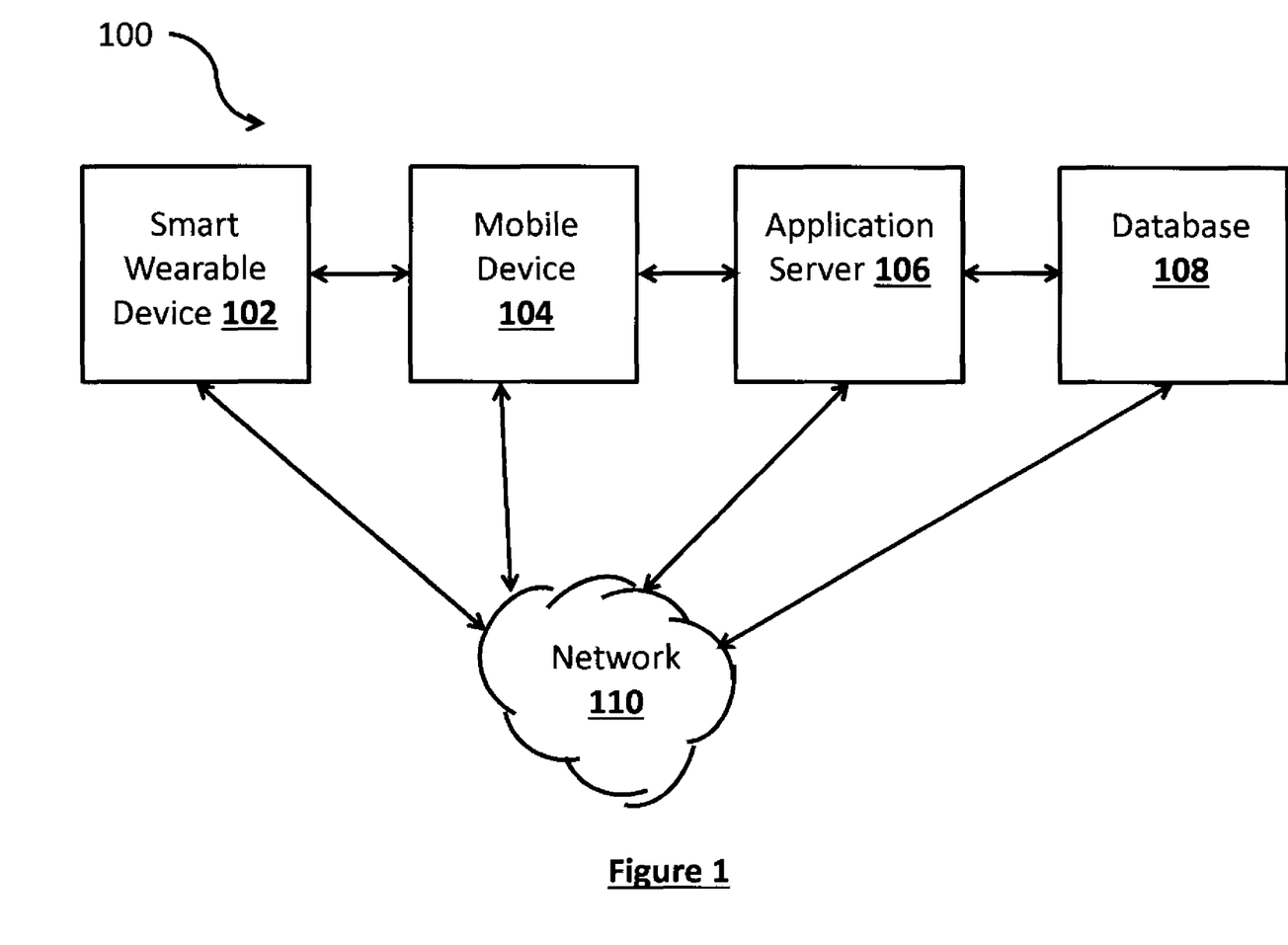
FIG. 1 illustrates a block diagram of a system level environment in accordance with an embodiment.

FIG. 1 shows a block diagram of system level environment in accordance with an embodiment of the present invention. The system 100 includes one or more smart wearable devices 102, one or more mobile devices 104, an application server 106 and a database 108 connected to each other through a communication network 110. The smart wearable device 102 may be any smart device which is capable of sending commands, instructions to the application server 106 and the mobile device 104. The smart wearable device 102 may include, but not limited to, a smart watch, smart fitness bands, smart shoes, smart glass, smart earphones/headphones, smart clothing, smart jewelry to name a few. The smart wearable device 102 may be connected to the application server 106 and the mobile device 104 through a radio communication network or Internet or short-range wireless communication methods like wife, Bluetooth, ZigBee, or Infrared transmission. The communication network 110 comprises a master and peripheral type of connection between the smart wearable device 102 and the mobile device 104. The communication network 106 may, for example be a radio network providing a short range, preferably between about 10 m-100 m, and more preferably up to 30 m of the smart wearable device and the mobile device to connect with each other. Further, the smart wearable device 102 may be connected either directly to the application server 106 or through the mobile device 104 (a mobile application is configured in the mobile device 104 which can receive inputs from smart wearable device 102, and the application server 106). The smart wearable device 102 is configured to track the activities body condition, and health-based parameters of a user. The health-based parameters include, but not limited to, optical, heat, pressure, sweat (liquid), blood pressure, heart rate, dizziness levels, BMI, movement of body parts, etc. associated with the user. In an embodiment, the mobile device 104 operates independently, and is configured to track the activities, body condition and health-based parameters of a user without the smart wearable device 102. In another embodiment, the smart wearable device 102, in operational interconnection with the mobile device 104, tracks the activities, body condition and health-based parameters of a user. The smart wearable device 102 and mobile device 104 may also be configured to track environmental parameters such as temperature, humidity level, moisture level, etc. The smart wearable device 102 communicates and transmits the details pertaining to the user activities, body condition, health based parameters to the mobile device 104 and application server 106. The data tracked and captured by the smart wearable device 102 and mobile device 104 is processed by the application server 106 and stored in database 108.

Figure 2:
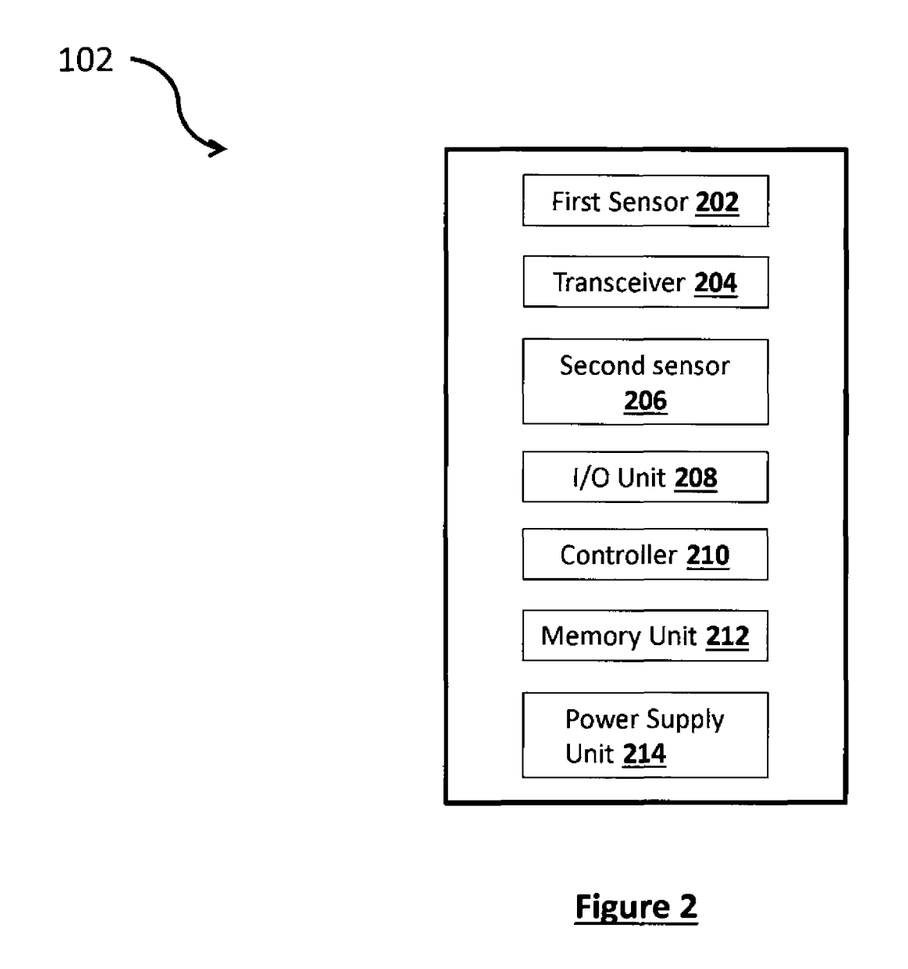
FIG. 2 illustrates a block diagram of a smart wearable device in accordance with an embodiment of the present invention.

FIG. 2 illustrates a block diagram of a smart wearable device 102 in accordance with an embodiment of the present invention. The smart wearable device 102 includes one or more first sensor 202 to track and capture optical, heat, pressure, sweat (liquid), heart rate etc. associated with the user. The first sensor 202 may include accelerometers, step-counters, temperature sensors, blood pressure sensors, heart rate sensors among others which capture various types of data associated with the user. The first sensors 102 may also contain suitable sensing elements for monitoring the environmental conditions such as pollutant level, temperature level, humidity level, moisture level, heat level etc. The data captured by the first sensor 202 is communicated through a transceiver 204 to the mobile device 104 and application server 106. Further, the smart wearable device 102 comprises a second sensor 206 for sensing user selection input, received via an I/O unit 208, which is captured by a controller 210 and is transmitted by the transceiver 204. The second sensor 206 may, for example be a touch sensing device, or a push button on a top surface or side of the smart wearable device 102, a biometric device, a gesture sensing device, a movement sensing device, a light sensing device or a sound sensing device among others. The user selection effects a change in voltage or current, which is captured by the controller 210 working in operational interconnection with the second sensor 206. The smart wearable device 102 also includes a memory unit 212 for storing data captured by various sensors. The commands for the operation of each of the smart wearable device 102 are pre-programmed in their respective memory unit 212. The smart wearable device 102 further includes a power supply unit 214 including a battery for supplying power to various modules/units of the smart wearable device 102.

Figure 3:
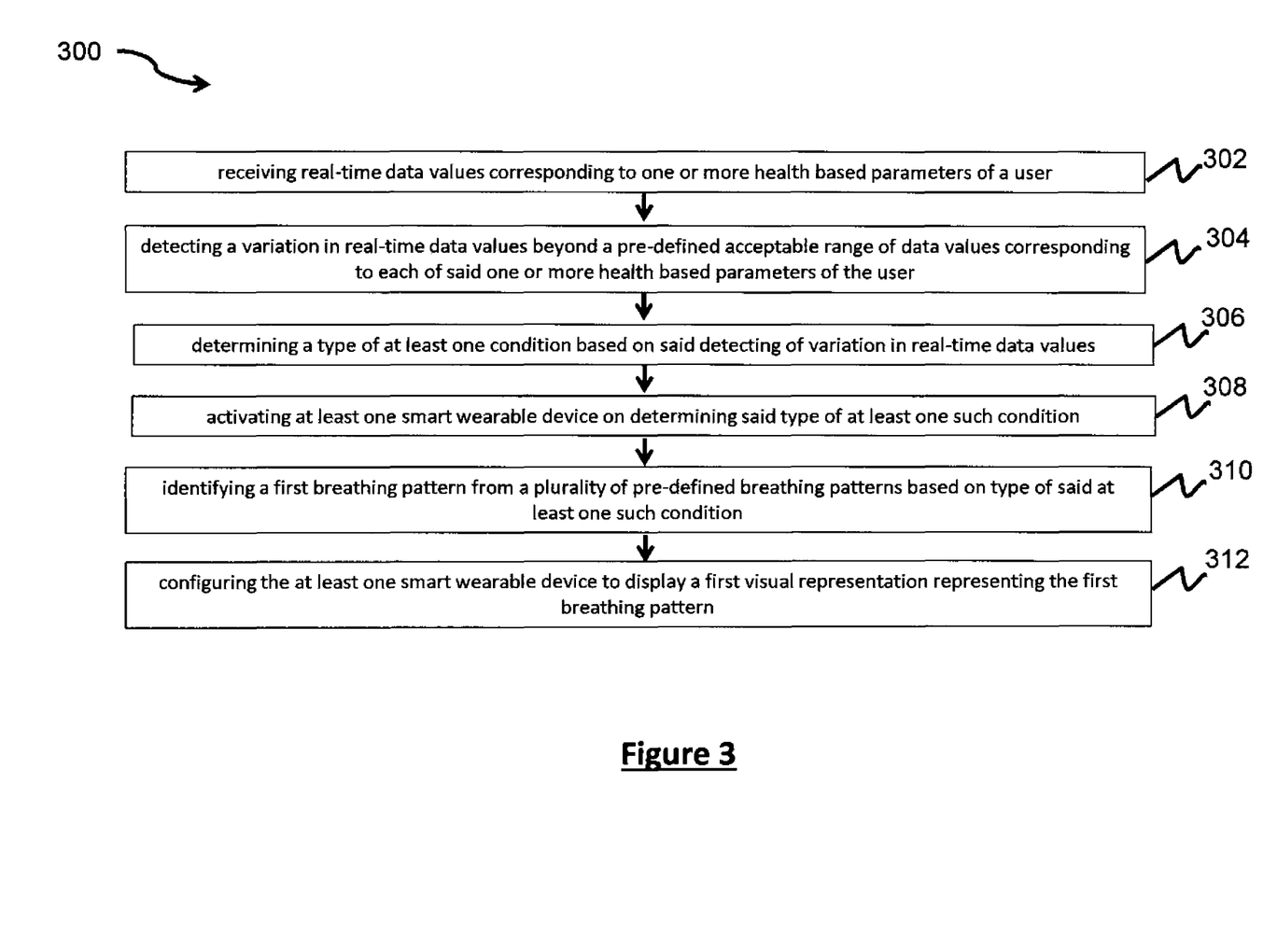
FIG. 3 is a flowchart illustrating a method for indicating a breathing pattern to a user in accordance with an embodiment of the present invention.

Referring to FIG. 3, a method for indicating a breathing pattern to a user in accordance with an embodiment of the present invention is provided. The method 300 includes step 302 of receiving real-time data values corresponding to one or more health-based parameters of a user. The one or more health-based parameters include parameters relating to optical, heat, pressure, sweat (liquid), blood pressure, heart rate, dizziness levels, BMI, etc. associated with the body conditions of the user. The health-based parameters also include parameters relating to movement of the body parts such as hands, eyes, legs, etc. The one or more first sensor 202 as referred in FIG. 2 may be used to monitor data values pertaining to the aforesaid parameters. The real-time data values corresponding to one or more health-based parameters of a user are compared with pre-defined acceptable range of data values corresponding to each of said one or more health-based parameters of the user to detect a variation from the said pre-defined acceptable range in step 304. On detecting variation in real-time data values from the said pre-defined acceptable range in step 304, the method 300 involves step 306 of determining a type of at least one condition (for example, a stressed condition) based on said detecting of variation in real-time data values. In an embodiment, the various types of conditions may include but not limited to, stress, fear, angry, unconsciousness, fatigue etc. For each such condition, the respective acceptable range is pre-defined and based on the detected real-time values and variations from the pre-defined acceptable range thereof, the appropriate condition may be determined and identified. In an implementation, only one health-based parameter may be sufficient to determine the type of condition. In another implementation, a plurality of parameters may be required and used to identify and determine the types of condition. Once such condition is determined, at least one smart wearable device is activated to identify a first breathing pattern from a plurality of pre-defined breathing patterns based on type of said at least one condition as indicated in steps 308 and 310 respectively. The first breathing pattern is identified such that the exercising of the selected first breathing pattern facilitates in bringing the real-time data values corresponding to said one or more health-based parameters within said pre-defined acceptable range. For instance, exercise of one of breathing pattern assists the user in controlling his present condition stress or anger or any other moods/which are nonessential and harmful for the health of the user. The user is required to synchronize his breathing rhythm with the breathing pattern to reduce the level of stress or angry feelings by controlling his breathing rhythm in accordance with the breathing pattern. The identified first breathing pattern is represented in the form of a visual representation on the display of the smart wearable device in step 312, wherein the first visual representation includes at least one of an hour hand, a minute hand and a second hand representing a watch, and wherein different cycles of a breath in the first breathing pattern are represented by rotation cycles of the at least one of the hour hand, the minute hand and the second hand respectively. The first visual representation may include an animated pattern of a smart watch in a manner such that hands of the smart watch or any watch are capable of rotating in both clockwise and anti-clockwise direction representing a breathing pattern to the user. In an exemplary implementation, any hands, such as chronographs hands, in addition to hour, minute and second hand may also be used for representing a breathing pattern.

In an embodiment, the first rotational direction of at least one of the hour hand, the minute hand and the second hand corresponds to an inhaling part of the first breathing pattern, wherein a second rotational direction of at least one of the hour hand, the minute hand and the second hand correspond to an exhaling part of the first breathing pattern. The inhaling and exhaling air relates to one cycle of breathing. The first rotational direction and second rotational direction are opposite in character. For instance, first rotational direction may correspond to a clockwise direction (rotation) of the hands and the second rotational direction may correspond to an anti-clockwise direction (rotation) of the hands.

In an embodiment, the non-movement of at least one of the hour hand, the minute hand and the second hand corresponds to the holding of the breath, while displaying the first breathing pattern. The duration of the non-movement of the at least one of the hour hand, the minute hand and the second hand is in accordance with the identified breathing pattern. For each breathing pattern, the timings, rotational speed are pre-configured and pre-set. The timing and speed of rotation cycles of the at least one of the hour hand, the minute hand and the second hand respectively are automatically adjusted based on the real-time data values corresponding to one or more health-based parameters and the selected first breathing pattern from the list of breathing patterns.

In an embodiment, the visual representation may involve change in the colour of the hands or dial to exhibit inhaling, exhaling part, breath holding of the breathing pattern. For instance, red colour of one hand may indicate inhaling part and green colour may indicate exhaling part. In another instance, the dial colour may be changed to red, indicating inhaling part and green colour indicating exhaling part. The colour change of the hands or dial provides the user to easily differentiate and understand various parts of a breathing exercise. In an exemplary implementation, inhaling part of the breathing pattern may be displayed by rotation of the hour hand to value 3 (indicating 3'o clock) in red colour. The red colour indicating that an inhaling part is to be exercised and positioning of the hour hand to value 3 indicating that inhaling part is to be performed 3 times. In another exemplary implementation, each single movement of the minute hand may correspond to the duration of the inhaling part or exhaling part. Various combinations with various hands and their rotations thereof, and numbers displayed on the watch, may be configured for the purposes of execution of at least one of breathing pattern corresponding to a breathing exercise.

In an embodiment, the first breathing pattern corresponds to a breathing exercise and wherein the breathing exercise is visually represented as a pattern, through movement and non-movement of the at least one of the hour hand, minute hand and the second hand or dial respectively. The breathing exercise is converted to number of clock cycles, matched appropriately with the clock hands, for its operation. The first breathing pattern corresponds to a breathing exercise selected from a group of breathing exercises comprising a breath control exercise (pranayama), a deep and slow breathing exercise (Bhastrika Pranayama), an alternate nostril breathing exercise (Anulom Vilom Pranayama), a cooling breath exercise (Sitali Pranayama), an ocean breath exercise (Ujjayi Pranayama), a breathing with humming sound exercise (Bhramari Pranayama), an equal Breathing exercise, an abdominal breathing exercise, and a skull shining breathing exercise. By exercising the appropriate breathing exercise, the various types of conditions may include but not limited to, stress, fear, angry, unconsciousness, fatigue etc., are normalized.

In another embodiment, the method 300 includes generating a first trigger to facilitate the user to initiate the inhaling part of the first breathing pattern; generating a second trigger to facilitate the user to initiate the exhaling part of the first breathing pattern; and generating a first trigger to facilitate the user to initiate the breath holding part of the first breathing pattern. The aforesaid triggers may be in the form of a notification made in the form of a textual or visual notification or a voice notification. In other words, the smart wearable device is configured to generate a trigger or alarm to notify the breathing pattern, a start time or breath holding part or an end time of the breathing pattern.

In another embodiment, the method 300 includes monitoring the real time values corresponding to said one or more health based parameters of the user after a pre-defined time interval of initiation of the first breathing exercise by the user; ascertaining if the real-time data values are reaching the pre-defined acceptable range; deactivating/stopping display of the first visual representation corresponding to the first breathing pattern being exercised by the user on negative ascertaining; displaying a new visual representation a new breathing pattern to be exercised by the user. In case the real-time data values are found to be reaching the pre-defined acceptable range, the same visual representation continues to be displayed on the smart wearable device. In an implementation, the user may be prompted with an alternative (new) visual representation if the user is finding it difficult to exercise a breathing exercise represented by an existing visual representation.

In another embodiment, the method 300 includes collecting historical medical data of the user; and defining acceptable range including threshold data values corresponding to each of said one or more health-based parameters based on said historical medical data of the user. For each user, the acceptable range may be different depending upon its historical medical data. The medical data relates to user data pertaining to weight, height, BMI, past medical history, past family medical history, diet habits, nature of occupation, gender, medicines intake history, allergic information and any other information relating to health. The acceptable range may also take into account the present environmental conditions of the user. For instance, the acceptable range for a same user may be different during a summer season and a winter season. The step 304 of detecting the variation in health-based parameters with real-time data values includes comparing the real-time data values corresponding to one or more health-based parameters of the user with pre-stored threshold data values corresponding to each of said one or more health-based parameters; and identifying a variation in the real-time data values corresponding to one or more health-based parameters based on such comparison.

In another embodiment, the method 300 includes defining one or more breathing patterns in respect of each of said at least one type of condition, wherein each of said condition is associated with a mood of the user; and defining at least one visual representation corresponding to each of said one or more breathing patterns.

In another embodiment, the method 300 includes receiving inputs from a plurality of gas sensors regarding presence of pollutants present within an environment surrounding the user; and configuring the at least one smart wearable device to display a second visual representation representing a second breathing pattern, wherein the second visual representation is different from the first visual representation, and wherein the second visual representation facilitates the user to control inhaling, exhaling and holding of breath based on the inputs from the plurality of gas sensors, in real time. For example, the gas sensors are configured to dynamically sense the environment and detect the gas levels, poisonous and other hazardous elements present in the environment. Subsequently, a determination is made as to a level of breathing or an amount of breath to be consumed by the user and the same is displayed to the user. Further, the gas sensors are capable of identifying different gases and quantities in the surrounding environment. For example, if the user is exposed to an environment which has a poor air quality (e.g., chemical exposure, laboratory conditions and the like), the smart wearable device is configured to alert the user regarding the poor air quality with quantity and activate an appropriate breathing pattern so that user can avoid excessive breathing in poor environmental conditions.

In one embodiment, the smart wearable device automatically activates a preset breathing pattern required to be followed by the user to reduce or normalize real time data values (adverse condition values) of the user. In an embodiment, the breathing pattern can be manually set by the user, or automatically set by the smart wearable device based on the user data.

In an embodiment, different visual representations corresponding to different breathing patterns are stored in the smart wearable device and may be referred to and used by the user at its will. The smart wearable device can display real-time variation (for example, percentage or graph) of health/mood/emotion index to the user. In an embodiment, the user may choose and store a preset list of breathing exercise for different conditions. The user can also manually store the duration of such breathing exercises or the smart wearable device is configured to automatically determine such duration (in seconds, minutes or hours) based on the user's real-time health index and past activities. For example, the smart wearable device is automatically activated when the user is stressed, the minute hand of smart wearable device may rotate clockwise (for step values, including but not limited to 0-60, 5, 10, 15, 20, 25, 30, 35, 40, 45, 50, 55 60 or any other equivalent preset step value), and hour hand shall rotate anti-clockwise (for step values, including but not limited to 0-60, 5, 10, 15, 20, 25, 30, 35, 40, 45, 50, 55 60 or any other equivalent preset step value) illustrating one of a breathing exercise appropriate for such stressed condition of the user.

Figure 4:
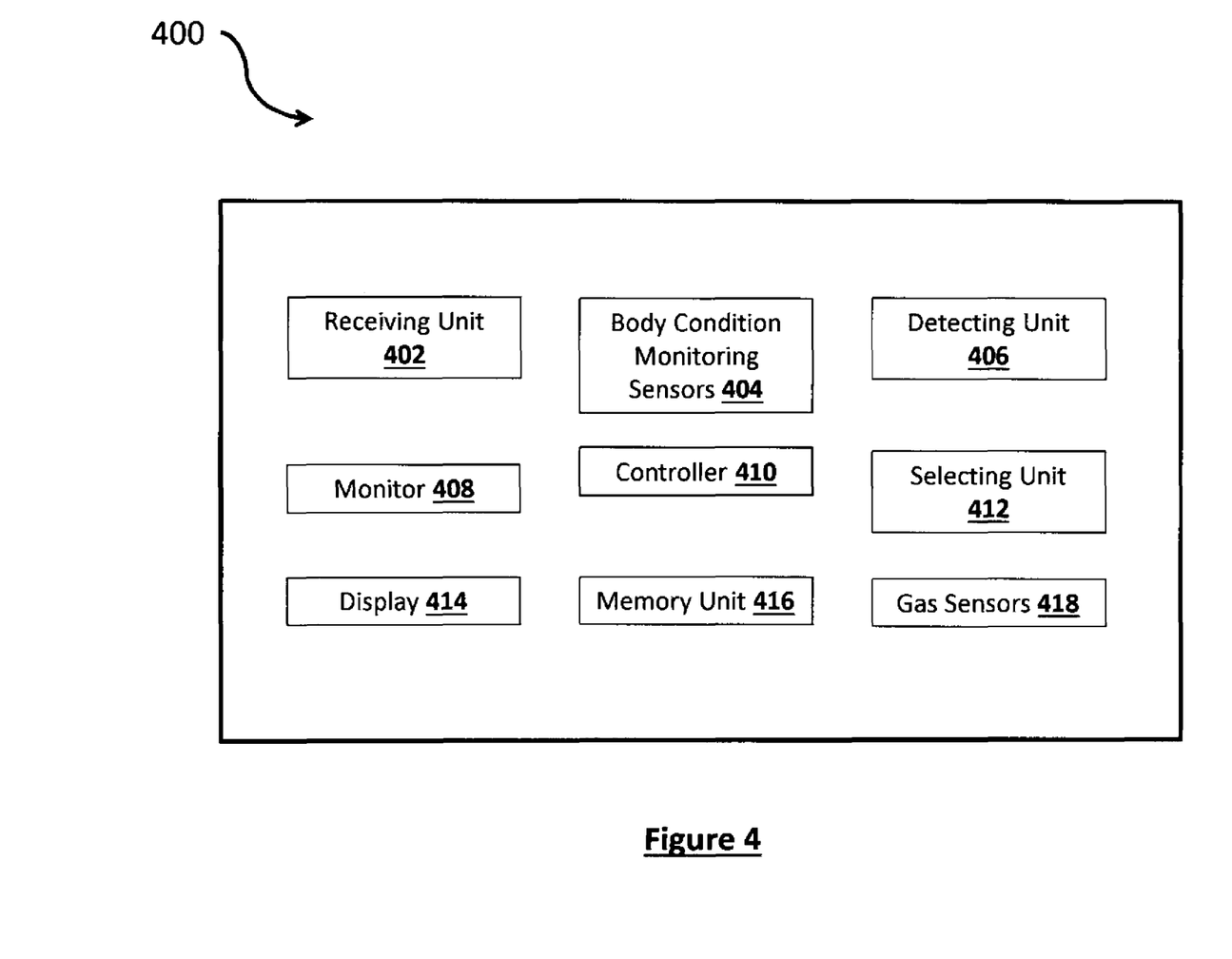
FIG. 4 illustrates a block diagram of a system for indicating a breathing pattern to a user in accordance with an embodiment of the present invention.

Referring to FIG. 4, a block diagram of a system for indicating a breathing pattern to a user in accordance with an embodiment of the present invention is provided. The system 400 includes a receiving unit 402 configured to receive real-time data values corresponding to one or more health-based parameters of a user. The one or more health-based parameters are sensed using body condition monitoring sensors 404 provided with sensing capabilities to sense health-based parameters relating to optical, heat, pressure, sweat (liquid), blood pressure, heart rate, dizziness levels, BMI, movement of body parts, etc. associated with the user. The body condition monitoring sensors 404 include, but not limited to, an optical sensor, a heat sensor, a pressure sensor, a sweat (liquid) sensor, a gyro, a touch sensor, a heart rate sensor and other sensors to measure the one or more parameters of the user. A detecting unit 406 is provided to detect a variation in real-time data values beyond a pre-defined acceptable range of data values corresponding to each of said one or more health-based parameters of the user. The detecting unit 406 compares the real-time data values with pre-defined acceptable range of data values (threshold values) corresponding to each of said one or more health-based parameters of the user to detect a variation thereof. Based on the detected variation, a monitor 408 determines a type of at least one condition. The various types of conditions may include but not limited to, stress, fear, angry, unconsciousness, fatigue etc. For each condition, the respective acceptable range is pre-defined and based on the detected real-time values and variations from the pre-defined acceptable range thereof, the appropriate condition is determined by the monitor 408. A controller 410 is further provided to activate at least one smart wearable device on determining a type of at least one condition by the monitor 408. Once the smart device is activated, the controller 410, in operational interconnection with a selecting unit 412, identifies a first breathing pattern from a plurality of pre-defined breathing patterns based on the determined condition, such that exercising of the first breathing pattern facilitates in bringing the real-time data values corresponding to said one or more health-based parameters within the pre-defined acceptable range. The first breathing pattern corresponds to a breathing exercise selected from a group of breathing exercises comprising a breath control exercise (pranayama), a deep and slow breathing exercise (Bhastrika Pranayama), an alternate nostril breathing exercise (Anulom Vilom Pranayama), a cooling breath exercise (Sitali Pranayama), an ocean breath exercise (Ujjayi Pranayama), a breathing with humming sound exercise (Bhramari Pranayama), an equal Breathing exercise, an abdominal breathing exercise, and a skull shining breathing exercise.

Once the appropriate first breathing pattern is identified, a first visual representation representing the first breathing pattern is displayed on the display 414, wherein the first visual representation includes at least one of an hour hand, a minute hand and a second hand representing a watch, and wherein different cycles of a breath in the first breathing pattern are represented by a pattern or rotation cycles of the at least one of the hour hand, the minute hand and the second hand respectively. The inhaling, exhaling and holding part of a first breathing pattern are exhibited by the rotational directions and movements of the various hands of the watch. For instance, rotation of one or more hands in clockwise direction may correspond to an inhaling part of the first breathing pattern, rotation of one or more hands in anti-clockwise direction may correspond to an exhaling part of the first breathing pattern, and non-movement of one or more hands may correspond to breath holding part of the first breathing pattern.

A memory unit 416 is provided to store the details pertaining to real time data values, various conditions relating to health, acceptable range corresponding to each type of conditions, details of various breathing patterns, execution instructions corresponding to the visual representation and instructions for controlling movement of the hands of the smart watch. The memory unit 416 further stores medical data corresponding to various users. In an embodiment, the subject medical data recorded in the smart wearable device is synchronized with the database, on timely basis. In another embodiment, the medical and health related data may be stored manually by the user or may be generated automatically based when the system 400 is configured to read the medical and health-related data of the user.

In an embodiment, the body condition monitoring sensors 404 are configured to determine a heart rate of the user and the controller 410 automatically activates display of a visual representation corresponding to an appropriate breathing pattern when the heart rate reaches a predetermined threshold value.

In another embodiment, the system 400 is configured to determine a taste satisfaction level of the user using the heart rate of the user. For example, the smart wearable device is configured to determine a variation pattern in the heart rate while the user is having a specific food and subsequently, the taste satisfaction level of the user is determined.

Further, the system 400 is configured to determine likability parameters of getting a heart attack. The smart wearable device is configured to monitor heart rate variations of the user, and automatically trigger the alarm when heart rate goes below such threshold values (which are determined for a person, based on his medical conditions) or any problem with pulse (heart beats) and any sudden variation in pulse due to one or more activities of the user.

In an embodiment, the system 400 is configured to identify critical medical conditions such as the heart attack and generate an alarm. In such conditions, the system 400 is configured to auto call an ambulance or a care taker for an emergency pickup of the user. The alert can include but is not limited to an alert message, a phone call, and a vibration based alert message to communicate to the user to perform one or more breathing exercises. Subsequent to the alert, the breathing pattern for the one or more breathing exercises is displayed to the user. The user is required to synchronize his breathing with the displayed breathing pattern of the one or more breathing exercises.

In an embodiment, the smart wearable device is configured to include at least bidirectional motors, independent hands, a Bluetooth module, accelerometer, magnetometer, and a vibrator.

In an embodiment, the receiving unit 402 is configured to receive inputs from a plurality of gas sensors 418, said plurality of gas sensors 418 configured to provide inputs regarding presence of pollutants/gas particles present within an environment surrounding the user. Based on the inputs received from the gas sensors 418, the controller 408 activates the at least one smart wearable device to display a second visual representation representing a second breathing pattern different from the first visual representation, and wherein the second visual representation facilitates the user to control inhaling, exhaling and holding of breath.

The disclosure offers several advantages. The methods and systems described herein enable the user to control his medical/health condition through controlling his breathing pattern. Based on a respective condition of the user, the methods and systems described herein requires the user to follow breathing patterns which are mandatory to address his health condition. As a result, the user finds himself at a relatively healthier and stress-free state.

Figure 5:
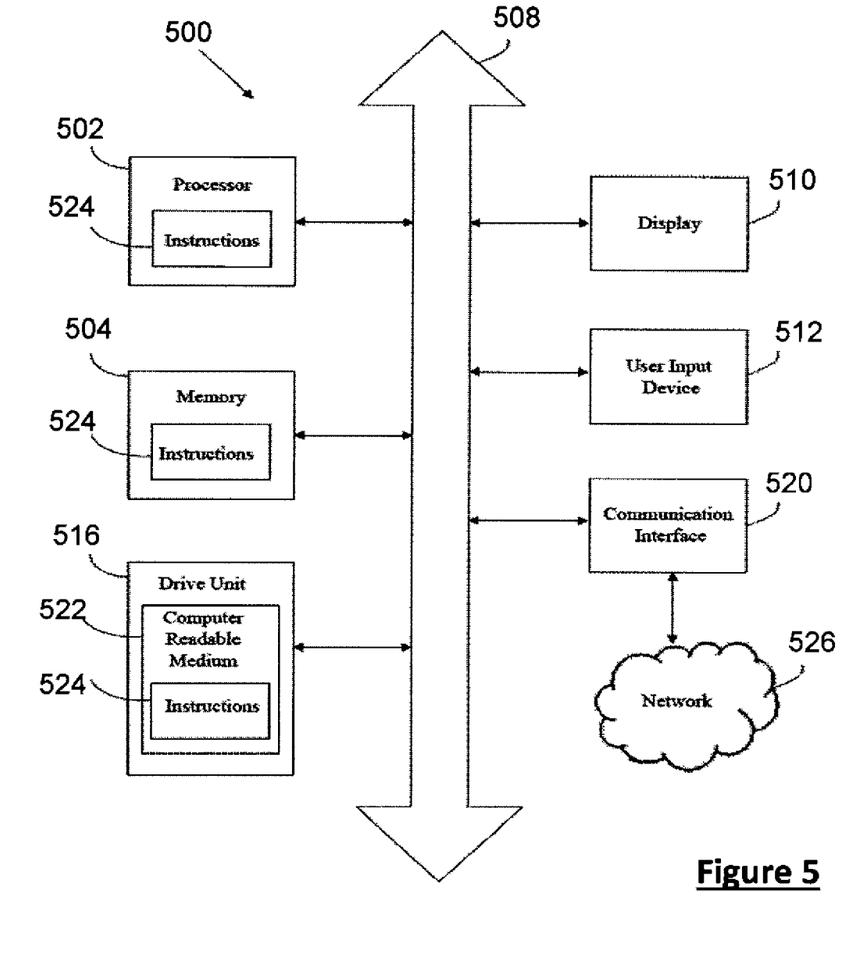
FIG. 5 illustrates a typical hardware configuration of a computer system, which is representative of a hardware environment for practicing the present invention.

Referring to FIG. 5, a typical hardware configuration of a computer system, which is representative of a hardware environment for practicing the present invention, is illustrated. The computer system 500 can include a set of instructions that can be executed to cause the computer system 500 to perform any one or more of the methods disclosed. The computer system 500 may operate as a standalone device or may be connected, e.g., using a network, to other computer systems or peripheral devices.

In a networked deployment, the computer system 500 may operate in the capacity of a server or as a client user computer in a server-client user network environment, or as a peer computer system in a peer-to-peer (or distributed) network environment. The computer system 500 can also be implemented as or incorporated into various devices, such as a personal computer (PC), a tablet PC, a personal digital assistant (PDA), a mobile device, a palmtop computer, a laptop computer, a desktop computer, a communications device, a wireless telephone, a land-line telephone, a control system, a camera, a scanner, a printer, a personal trusted device, a web appliance, a network router, switch or bridge, or any other machine capable of executing a set of instructions (sequential or otherwise) that specify actions to be taken by that machine. Further, while a single computer system 500 is illustrated, the term "system" shall also be taken to include any collection of systems or sub-systems that individually or jointly execute a set, or multiple sets, of instructions to perform one or more computer functions.

The computer system 500 may include a processor 502 e.g., a central processing unit (CPU), a graphics processing unit (GPU), or both. The processor 502 may be a component in a variety of systems. For example, the processor may be part of a standard personal computer or a workstation. The processor 502 may be one or more general processors, digital signal processors, application specific integrated circuits, field programmable gate arrays, servers, networks, digital circuits, analog circuits, combinations thereof, or other now known or later developed devices for analysing and processing data. The processor 502 may implement a software program, such as code generated manually (i.e., programmed).

The computer system 500 may include a memory 504, such as a memory 504 that can communicate via a bus 508. The memory 504 may be a main memory, a static memory, or a dynamic memory. The memory 504 may include, but is not limited to computer readable storage media such as various types of volatile and non-volatile storage media, including but not limited to random access memory, read-only memory, programmable read-only memory, electrically programmable read-only memory, electrically erasable read-only memory, flash memory, magnetic tape or disk, optical media and the like. In one example, the memory 504 includes a cache or random-access memory for the processor 502. In alternative examples, the memory 504 is separate from the processor 502, such as a cache memory of a processor, the system memory, or other memory. The memory 504 may be an external storage device or database for storing data. Examples include a hard drive, compact disc ("CD"), digital video disc ("DVD"), memory card, memory stick, floppy disc, universal serial bus ("USB") memory device, or any other device operative to store data. The memory 504 is operable to store instructions executable by the processor 502. The functions, acts or tasks illustrated in the figures or described may be performed by the programmed processor 502 executing the instructions stored in the memory 504. The functions, acts or tasks are independent of the particular type of instructions set, storage media, processor or processing strategy and may be performed by software, hardware, integrated circuits, firm-ware, microcode and the like, operating alone or in combination. Likewise, processing strategies may include multiprocessing, multitasking, parallel processing and the like.

As shown, the computer system 500 may or may not further include a display unit 510, such as a liquid crystal display (LCD), an organic light emitting diode (OLED), a flat panel display, a solid-state display, a cathode ray tube (CRT), a projector, a printer or other now known or later developed display device for outputting determined information. The display 510 may act as an interface for the user to see the functioning of the processor 502, or specifically as an interface with the software stored in the memory 504 or in the drive unit 516.

Additionally, the computer system 500 may include an input device 512 configured to allow a user to interact with any of the components of system 500. The input device 512 may be a number pad, a keyboard, or a cursor control device, such as a mouse, or a joystick, touch screen display, remote control or any other device operative to interact with the computer system 500.

The computer system 500 may also include a disk or optical drive unit 516. The disk drive unit 616 may include a computer-readable medium 522 in which one or more sets of instructions 524, e.g. software, can be embedded. Further, the instructions 524 may embody one or more of the methods or logic as described. In a particular example, the instructions 524 may reside completely, or at least partially, within the memory 504 or within the processor 502 during execution by the computer system 500. The memory 504 and the processor 502 also may include computer-readable media as discussed above.

The present invention contemplates a computer-readable medium that includes instructions 524 or receives and executes instructions 524 responsive to a propagated signal so that a device connected to a network 526 can communicate voice, video, audio, images or any other data over the network 526. Further, the instructions 524 may be transmitted or received over the network 526 via a communication port or interface 520 or using a bus 508. The communication port or interface 520 may be a part of the processor 502 or may be a separate component. The communication port 520 may be created in software or may be a physical connection in hardware. The communication port 520 may be configured to connect with a network 526, external media, the display 510, or any other components in system 500 or combinations thereof. The connection with the network 526 may be a physical connection, such as a wired Ethernet connection or may be established wirelessly as discussed later. Likewise, the additional connections with other components of the system 500 may be physical connections or may be established wirelessly. The network 526 may alternatively be directly connected to the bus 508.

The network 526 may include wired networks, wireless networks, Ethernet AVB networks, or combinations thereof. The wireless network may be a cellular telephone network including GSM, GPRS, 3G, EVDO, mesh, or other networks type, an 802.11, 802.16, 802.20, 802.1Q or WiMax network. Further, the network 526 may be a public network, such as the Internet, a private network, such as an intranet, or combinations thereof, and may utilize a variety of networking protocols now available or later developed including, but not limited to TCP/IP based networking protocols.

In an alternative example, dedicated hardware implementations, such as application specific integrated circuits, programmable logic arrays and other hardware devices, can be constructed to implement various parts of the system 500.

Applications that may include the systems can broadly include a variety of electronic and computer systems. One or more examples described may implement functions using two or more specific interconnected hardware modules or devices with related control and data signals that can be communicated between and through the modules, or as portions of an application-specific integrated circuit. Accordingly, the present system encompasses software, firmware, and hardware implementations.

The system described may be implemented by software programs executable by a computer system. Further, in a non-limited example, implementations can include distributed processing, component/object distributed processing, and parallel processing. Alternatively, virtual computer system processing can be constructed to implement various parts of the system.

The system is not limited to operation with any particular standards and protocols. For example, standards for Internet and other packet switched network transmission (e.g., TCP/IP, UDP/IP, HTML, HTTP) may be used. Such standards are periodically superseded by faster or more efficient equivalents having essentially the same functions. Accordingly, replacement standards and protocols having the same or similar functions as those disclosed are considered equivalents thereof.

The method steps of the implementations described herein are intended to include any suitable method of causing such method steps to be performed, consistent with the patentability of the following claims, unless a different meaning is expressly provided or otherwise clear from the context. So, for example performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

The drawings and the forgoing description give examples of embodiments. Those skilled in the art will appreciate that one or more of the described elements may well be combined into a single functional element. Alternatively, certain elements may be split into multiple functional elements. Elements from one embodiment may be added to another embodiment. For example, orders of processes described herein may be changed and are not limited to the manner described herein. Moreover, the actions of any flow diagram need not be implemented in the order shown; nor do all of the acts necessarily need to be performed. Also, those acts that are not dependent on other acts may be performed in parallel with the other acts. The scope of embodiments is by no means limited by these specific examples. Numerous variations, whether explicitly given in the specification or not, such as differences in structure, dimension, and use of material, are possible. The scope of embodiments is at least as broad as given by the following claims.

I claim:

1. A method for indicating a breathing pattern, the method comprising:
   receiving real-time data values corresponding to one or more health-based parameters of a user;
   detecting a variation in the real-time data values beyond a pre-defined acceptable range of data values corresponding to each of the one or more health-based parameters of the user;
   determining a type of at least one condition based on the variation in real-time data values as detected;
   activating at least one smart wearable device on determining the type of the at least one condition;
   identifying a first breathing pattern from a plurality of pre-defined breathing patterns based on type of the at least one condition as a breathing pattern that facilitates in bringing the real-time data values corresponding to the one or more health-based parameters within the pre-defined acceptable range;
   pre-configuring and pre-setting, for the first breathing pattern, a timing and a speed of rotation cycles of at least one of an hour hand, a minute hand, and a second hand to represent a watch;
   configuring the at least one smart wearable device to display a first visual representation representing the first breathing pattern, wherein the first visual representation comprises the at least one of the hour hand, the minute hand, and the second hand representing the watch, wherein different cycles of a breath in the first breathing pattern are represented by rotation cycles of the at least one of the hour hand, the minute hand, and the second hand;
   automatically adjusting, based on the real-time data values corresponding to the one or more health-based parameters and the first breathing pattern, the timing and the speed of the rotation cycles of the at least one of the hour hand, the minute hand, and the second hand; and
   changing a color of the at least one of the hour hand, the minute hand, and the second hand, and dial color based on the first breathing pattern, wherein the different cycles of the breath in the first breathing pattern are represented by different colors of the at least one of the hour hand, the minute hand, and the second hand.

2. The method as claimed in claim 1, wherein:
   the at least one smart wearable device is configured to display a first rotational direction of at least one of the hour hand, the minute hand, and the second hand corresponding to an inhaling part of the first breathing pattern;
   the at least one smart wearable device is configured to display a second rotational direction of at least one of the hour hand, the minute hand, and the second hand corresponding to an exhaling part of the first breathing pattern; and
   the at least one smart wearable device is configured to display non-movement of at least one of the hour hand, the minute hand, and the second hand that corresponds to holding of the breath between the inhaling and exhaling part of first breathing pattern, while displaying the first breathing pattern.

3. The method as claimed in claim 2, further comprising:
   generating a first trigger to facilitate the user to initiate the inhaling part of the first breathing pattern;
   generating a second trigger to facilitate the user to initiate the exhaling part of the first breathing pattern; and generating a third trigger to facilitate the user to initiate the breath holding part of the first breathing pattern.

4. The method as claimed in claim 1, wherein:
the first breathing pattern corresponds to a breathing exercise;
the breathing exercise is visually represented as a pattern, through movement and non-movement of the at least one of the hour hand, the minute hand, and the second hand; and
the first breathing pattern is selected from a group of breathing exercises consisting of: a breath control exercise, a deep and slow breathing exercise, an alternate nostril breathing exercise, a cooling breath exercise, an ocean breath exercise, a breathing with humming sound exercise, an equal breathing exercise, an abdominal breathing exercise, and a skull shining breathing exercise.

5. The method as claimed in claim 1, further comprising:
collecting historical medical data of the user; and
defining an acceptable range comprising threshold data values corresponding to each of the one or more health-based parameters based on the historical medical data of the user.

6. The method as claimed in claim 5, wherein detecting the variation in health-based parameters with real-time data values comprises:
performing the comparison between the real-time data values corresponding to one or more health-based parameters of the user with the threshold data values corresponding to each of the one or more health-based parameters; and
identifying the variation in the real-time data values corresponding to one or more health-based parameters based on comparison.

7. The method as claimed in claim 5, wherein the historical medical data comprises at least a combination of: weight; height; body mass index (BMI), real-time heart rate, fatigue, stress, real-time blood pressure, dizziness levels, past medical history, past family medical history, diet habits, nature of occupation, gender, medicines intake history, and allergic information.

8. The method as claimed in claim 1, further comprising:
defining the pre-defined breathing patterns in respect of each of the types of the at least one condition, wherein the at least one condition is associated with a mood of the user; and
defining at least one visual representation corresponding to each of the one or more breathing patterns.

9. The method as claimed in claim 1, further comprising:
receiving inputs from a plurality of gas sensors regarding presence of pollutants present within an environment surrounding the user; and
configuring the at least one smart wearable device to display a second visual representation representing a second breathing pattern, wherein the second visual representation is different from the first visual representation, and wherein the second visual representation facilitates the user to control inhaling, exhaling, and holding of breath based on the inputs from the plurality of gas sensors, in real-time.

10. The method as claimed in claim 1, wherein the pre-defined acceptable range is determined based at least in part on a present environmental condition of the user.

11. The method as claimed in claim 10, wherein the present environmental condition of the user comprises at least one season.

12. The method as claimed in claim 1, further comprising:
monitoring the real-time data values corresponding to the one or more health-based parameters of the user after a pre-defined time interval of initiation of the first breathing exercise by the user;
ascertaining if the real-time data values are reaching the pre-defined acceptable range;
stopping display of the first visual representation corresponding to the first breathing pattern being exercised by the user on the real-time data values not reaching the pre-defined acceptable range; and
displaying a new visual representation having a new breathing pattern to be exercised by the user.

13. The method as claimed in claim 1, further comprising:
monitoring the real-time data values corresponding to the one or more health-based parameters of the user after a pre-defined time interval of initiation of the first breathing exercise by the user;
ascertaining if the real-time data values are reaching the pre-defined acceptable range;
stopping display of the first visual representation corresponding to the first breathing pattern being exercised by the user on the real-time data values not reaching the pre-defined acceptable range; and
prompting the user to select a new visual representation of a new breathing pattern to be exercised by the user;
in response to a selection of the new visual representation of the new breathing pattern, displaying the new visual representation having the new breathing pattern to be exercised by the user.

14. A system for indicating a breathing pattern, the system comprising:
at least one computing device comprising at least one hardware processor; and
program instructions stored in memory and executable in the at least one computing device that, when executed, directs the at least one computing device to:
receive real-time data values corresponding to one or more health-based parameters of a user;
detect a variation in the real-time data values beyond a pre-defined acceptable range of data values corresponding to each of the one or more health-based parameters of the user;
determine a type of at least one condition based on the variation in the real-time data values as detected;
activate at least one smart wearable device on the type of the at least one condition as determined;
identify a first breathing pattern from a plurality of pre-defined breathing patterns based on type of the at least one condition as a breathing pattern that facilitates in bringing the real-time data values corresponding to the one or more health-based parameters within the pre-defined acceptable range;
pre-configure and pre-set, for the first breathing pattern, a timing and a speed of rotation cycles of at least one of an hour hand, a minute hand, and a second hand to represent a watch;
direct the at least one smart wearable device to display a first visual representation representing the first breathing pattern, wherein the first visual representation comprises the at least one of the hour hand, the minute hand, and the second hand representing the watch, wherein different cycles of a breath in the first breathing pattern are represented by rotation cycles of the at least one of the hour hand, the minute hand, and the second hand;

automatically adjust, based on the real-time data values corresponding to the one or more health-based parameters and the first breathing pattern, the timing and the speed of the rotation cycles of the at least one of the hour hand, the minute hand, and the second hand; and change a color of the at least one of the hour hand, the minute hand, and the second hand based on the first breathing pattern, wherein the different cycles of the breath in the first breathing pattern are represented by different colors of the at least one of the hour hand, the minute hand, and the second hand.

15. The system as claimed in claim 14, wherein:

the at least one smart wearable device is directed to display a first rotational direction of at least one of the hour hand, the minute hand, and the second hand corresponding to an inhaling part of the first breathing pattern;

the at least one smart wearable device is directed to display a second rotational direction of at least one of the hour hand, the minute hand, and the second hand corresponding to an exhaling part of the first breathing pattern; and the at least one smart wearable device is directed to display non-movement of at least one of the hour hand, the minute hand, and the second hand that corresponds to holding of the breath between the inhaling and exhaling part of first breathing pattern, while the first breathing pattern is displayed.

16. The system as claimed in claim 14, wherein the at least one computing device is further directed to:

receive inputs from a plurality of gas sensors regarding presence of pollutants present within an environment surrounding the user; and configure the at least one smart wearable device to display a second visual representation representing a second breathing pattern, wherein the second visual representation is different from the first visual representation, and wherein the second visual representation facilitates the user to control inhaling, exhaling, and holding of breath based on the inputs from the plurality of gas sensors, in real-time.

17. A method for indicating a breathing pattern, the method comprising:

receiving real-time data values corresponding to a plurality of health-based parameters of a user of a smart wearable device comprising a plurality of sensors, the plurality of health-based parameters comprising at least two of: an optical parameter, a heat parameter, a pressure parameter, a sweat parameter, a blood pressure parameter, a heart rate parameter, a dizziness level parameter, a body mass (BM) parameter, and a body part movement parameter;

detecting a variation in the real-time data values beyond a pre-defined acceptable range of data values corresponding to each of the one or more health-based parameters of the user;

determining a type of a condition based on the variation in real-time data values as detected, the type of the condition being at least one of stress, fear, anger, unconsciousness, and fatigue;

activating the smart wearable device on determining the type of the condition;

storing a plurality of pre-defined breathing patterns in memory of the smart wearable device in associated with a plurality of different user conditions;

displaying the plurality of pre-defined breathing patterns in a display device of the smart wearable device;

suggesting a breathing pattern from the plurality of pre-defined breathing patterns based on type of the condition as a breathing pattern that facilitates in bringing the real-time data values corresponding to the one or more health-based parameters within the pre-defined acceptable range;

receiving a selection of the breathing pattern from a list comprising the plurality of pre-defined breathing patterns in the display device;

pre-configuring and pre-setting, for the breathing pattern, a timing and a speed of rotation cycles of at least one of an hour hand, a minute hand, and a second hand to represent a watch;

directing the smart wearable device to display a visual representation representing the breathing pattern, wherein the visual representation comprises the at least one of the hour hand, the minute hand, and the second hand representing the watch, wherein different cycles of a breath in the breathing pattern are represented by rotation cycles of the at least one of the hour hand, the minute hand, and the second hand, wherein:

the smart wearable device is directed to display a first rotational direction of at least one of the hour hand, the minute hand, and the second hand corresponding to an inhaling part of the breathing pattern;

the smart wearable device is directed to display a second rotational direction, opposite the first rotational direction, of at least one of the hour hand, the minute hand, and the second hand corresponding to an exhaling part of the breathing pattern; and the smart wearable device is directed to display non-movement of at least one of the hour hand, the minute hand, and the second hand corresponds to holding of the breath between the inhaling and exhaling part of the breathing pattern, while displaying the breathing pattern;

automatically adjusting, based on the real-time data values corresponding to the one or more health-based parameters and the breathing pattern, the timing and the speed of the rotation cycles of the at least one of the hour hand, the minute hand, and the second hand;

changing a color of the at least one of the hour hand, the minute hand, and the second hand based on the first breathing pattern, wherein the different cycles of the breath in the first breathing pattern are represented by different colors of the at least one of the hour hand, the minute hand, and the second hand; and directing the smart wearable device to display a real-time variation of at least one of a health index, a mood index, and an emotion index, wherein the real-time variation is displayed as a percentage or a graph.

18. The method as claim in claim 17, wherein the plurality of sensors comprises at least a combination of: an optical sensor, a heat sensor, a pressure sensor, a sweat sensor, a gyro, a touch sensor, and a heart rate sensor.

19. The method as claimed in claim 17, further comprising:

receiving inputs from a plurality of gas sensors regarding presence of pollutants present within an environment surrounding the user; and configuring the at least one smart wearable device to display a second visual representation representing a second breathing pattern, wherein the second visual representation is different from the first visual representation, and wherein the second visual representation facilitates the user to control inhaling, exhaling, and holding of breath based on the inputs from the plurality of gas sensors, in real-time.

* * * * *